United States Patent
Lin-Shiau et al.

(10) Patent No.: US 9,011,945 B2
(45) Date of Patent: Apr. 21, 2015

(54) COMPOSITION AND METHOD FOR NEUROPROTECTION AGAINST EXCITOTOXIC INJURY

(71) Applicant: National Taiwan University, Taipei (TW)

(72) Inventors: Shoei-Yn Lin-Shiau, Taipei (TW); Jen-Kun Lin, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 14/095,388

(22) Filed: Dec. 3, 2013

(65) Prior Publication Data

US 2014/0094513 A1 Apr. 3, 2014

Related U.S. Application Data

(60) Division of application No. 13/349,540, filed on Jan. 12, 2012, now abandoned, which is a continuation-in-part of application No. 12/243,655, filed on Oct. 1, 2008, now abandoned.

(51) Int. Cl.
| | |
|---|---|
| *A61K 36/82* | (2006.01) |
| *A61K 36/185* | (2006.01) |
| *A61K 31/353* | (2006.01) |
| *A61K 31/047* | (2006.01) |
| *A61K 31/13* | (2006.01) |
| *A61K 45/06* | (2006.01) |

(52) U.S. Cl.
CPC .............. *A61K 31/353* (2013.01); *A61K 31/047* (2013.01); *A61K 31/13* (2013.01); *A61K 45/06* (2013.01)

(58) Field of Classification Search
CPC ........................... A61K 2300/00; A61K 45/06
USPC ......................................................... 424/725
See application file for complete search history.

(56) References Cited

U.S. PATENT DOCUMENTS

2002/0151506 A1* 10/2002 Castillo et al. ................... 514/27
2008/0175909 A1* 7/2008 Vergez et al. ................... 424/468

OTHER PUBLICATIONS

Vickers (A Vaccine Against Alzheimer's Disease, Drug Aging 2002:19(2) 487-494).*

* cited by examiner

*Primary Examiner* — Chris R Tate
*Assistant Examiner* — Randall Winston
(74) *Attorney, Agent, or Firm* — Hannah M. Tien

(57) ABSTRACT

The present invention discloses the combined treatment of memantine (N-methyl-D-aspartate receptor antagonist) and tea polyphenol (an antioxidant and anti-inflammatory agent) is more effective (synergistic) in neuroprotection than either memantine or tea polyphenol alone in mouse excitotoxic injury. These findings provide useful information about the potential application of memantine and tea polyphenols in preventing or treating clinical excitotoxic injury such as brain trauma, brain ischemia, epilepsy, and Alzheimer's disease.

6 Claims, 11 Drawing Sheets

COMPOSITION AND METHOD FOR NEUROPROTECTION AGAINST EXCITOTOXIC INJURY

CROSS-REFERENCE TO RELATED APPLICATIONS

This application is a divisional of the pending U.S. patent application Ser. No. 13/349,540 filed on Jan. 12, 2012, which is a Continuation-in-part of the pending U.S. patent application Ser. No. 12/243,655 filed on Oct. 1, 2008, for which priority is claimed and is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention relates to a composition and a method for synergistic neuroprotection against excitotoxic injury.

BACKGROUND OF THE INVENTION

Glutamate is the main excitatory neurotransmitter in the mammalian central nervous system (CNS) and mediates neurotransmission in most excitatory synapses. Three classes of glutamate-gated ion channel receptors—α-amino-3-hydroxy-5-methyl-4-isoxazole propionic acid (AMPA), kainite, and N-methyl-D-aspartate (NMDA) receptors—can transduce postsynaptic signals. Among them, NMDA receptors are the most abundant and ubiquitously distributed throughout the brain. Therefore, they are fundamental to excitatory neurotransmission and critical for the maintenance of normal CNS function. However, excessive glutamate overstimulates NMDA receptors, leading to increased intracellular calcium and excitotoxicity (Kemp J A, McKernan R M. 2002. NMDA receptor pathways as drug targets. Nat Neurosci 5: 1039-1042.). It is by the glutamate-dependent mechanism that neurons die in various CNS disorders, including brain ischemia, epilepsy, and Alzheimer's disease. The role of NMDA receptors in excitotoxicity has driven the search for antagonists as neuroprotective agents.

On the other hand, NMDA receptor activity is essential for normal neuronal function. Potential neuroprotective agents that block virtually all NMDA receptor activity lead to unacceptable clinical side effects (drowsiness, hallucination, and even coma) because they block normal NMDA receptor activity (Palmer G C. 2001. Neuroprotection by NMDA receptor antagonists in a variety of neuropathologies. Curr Drug Targets 2: 241-271.). For this reason, many previous NMDA receptor antagonists have failed advanced clinical trials in a number of neurodegenerative disorders. In contrast, some studies have shown that the adamantane derivative memantine can block excessive NMDA receptor activity without disrupting normal activity and shows promise in clinical applications (Chen H S, Lipton S A. 2006. The chemical biology of clinically tolerated NMDA receptor antagonists. J Neurochem 97: 1611-1626.). Memantine exerts its pharmacological effects through its action as a low-affinity, uncompetitive open-channel blocker. Memantine has unique blocking sites in channel pores, and this subtle difference between memantine and other traditional NMDA receptor antagonists may explain many advantageous properties of memantine action. In fact, in normal conditions, the excitatory postsynaptic current resulting from physiological activation of NMDA receptors is mostly preserved. In excitotoxic conditions, when prolonged activation of NMDA receptors occurs, memantine becomes a very effective blocker. In essence, the pharmacological effects of memantine are most obvious under pathological conditions, and it maintains the normal functions of receptors, thus relatively sparing synaptic transmission and preserving long-term potentiation and maintaining physiological function (Chen H S, Wang Y F, Rayudu P V, Edgecomb P, Neill J C, Segal M M, Lipton S A, Jensen F E. 1998a. Neuroprotective concentrations of the N-methyl-D-aspartate open-channel blocker memantine are effective without cytoplasmic vacuolation following post-ischemic administration and do not block maze learning or long-term potentiation. Neuroscience 86: 1121-1132.). In fact, memantine has been used clinically with an excellent safety record for more than 20 years in Europe to treat Parkinson's disease, spasticity, convulsions, vascular dementia, and Alzheimer's disease.

NMDA receptors are involved in neuronal survival and maturation (Marshall J, Dolan B M, Garcia E P, Sathe S, Tang X, Mao Z, Blair L A. 2003. Calcium channel and NMDA receptor activities differentially regulate nuclear C/EBPbeta levels to control neuronal survival. Neuron 39: 625-639.), neuronal migration (Komuro H, Rakic P. 1993. Modulation of neuronal migration by NMDA receptors. Science 260: 95-97.; Kihara M, Yoshioka H, Hirai K, Hasegawa K, Kizaki Z, Sawada T. 2002. Stimulation of N-methyl-D-aspartate (NMDA) receptors inhibits neuronal migration in embryonic cerebral cortex: a tissue culture study. Brain Res Dev Brain Res 138: 195-198.), induction of long-term potentiation (Bliss T V, Collingridge G L. 1993. A synaptic model of memory: long-term potentiation in the hippocampus. Nature 361: 31-39.; Zhao J P, Phillips M A, Constantine-Paton M. 2006. Long-term potentiation in the juvenile superior colliculus requires simultaneous activation of NMDA receptors and L-type $Ca^{2+}$ channels and reflects addition of newly functional synapses. J Neurosci 26: 12647-12655.), formation of sensory maps (Simon D K, Prusky G T, O'Leary D D, Constantine-Paton M. 1992. N-methyl-D-aspartate receptor antagonists disrupt the formation of a mammalian neural map. Proc Natl Acad Sci USA 89: 10593-10597.), and neurodegeneration (Cull-Candy S, Brickley S, Farrant M. 2001. NMDA receptor subunits: diversity, development and disease. Curr Opin Neurobiol 11: 327-335.; Zieminska E, Stafiej A, Lazarewicz J W. 2003. Role of group I metabotropic glutamate receptors and NMDA receptors in homocysteine-evoked acute neurodegeneration of cultured cerebellar granule neurones. Neurochem Int 43: 481-492.). Under normal conditions of synaptic transmission, the NMDA receptor channel is gated by extracellular $Mg^{2+}$ sitting in the channel and only activated for brief periods. This brief opening of the NMDA receptors allows $Ca^{2+}$ (and other cations) to move into the cell for the subsequent physiological functions. Under pathological conditions, however, overactivation of the receptor relieves the $Mg^{2+}$ block and causes an excessive amount of $Ca^{2+}$ influx into the nerve cell, which in turn triggers a variety of processes that can lead to necrosis, apoptosis, or dendritic/synaptic damage. These detrimental processes include: (1) $Ca^{2+}$ overload of mitochondria, resulting in oxygen free-radical formation, activation of caspases, and release of apoptosis-inducing factor; (2) $Ca^{2+}$-dependent activation of neuronal NOS, leading to increased NO production and formation of toxic peroxynitrite (ONOO—) and S-nitrosylated glyceraldehyde-3-phosphate dehydrogenase (GAPDH); and (3) stimulation of mitogen-activated protein kinase p38, which activates transcription factors that can go into the nucleus to influence neuronal injury and apoptosis (Chen H S, Lipton S A. 2006. The chemical biology of clinically tolerated NMDA receptor antagonists. J Neurochem 97: 1611-1626.).

In excitotoxic conditions, mitochondrial dysfunction associated with loss of $Ca^{2+}$ homeostasis and enhanced cellular oxidative stress plays a major role in cell damage (Frandsen A, Schousboe A. 1993. Excitatory amino acid-mediated cytotoxicity and calcium homeostasis in cultured neurons. J Neurochem 60: 1202-1211.; Jacquard C, Trioulier Y, Cosker F, Escartin C, Bizat N, Hantraye P, Cancela J M, Bonvento G, Brouillet E. 2006. Brain mitochondrial defects amplify intracellular $[Ca^{2+}]$ rise and neurodegeneration but not $Ca^{2+}$ entry during NMDA receptor activation. FASEB J 20: 1021-1023.). Under these circumstances, stimulation of ionotropic glutamate receptors causes massive $Ca^{2+}$ entry and is highly involved in the process of neuronal death. Energy depletion and increased oxidative damage to several synaptic proteins such as $Na^+$, $K^+$-ATPase may result in loss of local $Ca^{2+}$ homeostasis and membrane depolarization. As a consequence, synaptic degeneration follows. In addition, $Ca^{2+}$ is known to activate several intracellular enzymes, such as phospholipase A2, nitric oxide synthase, xanthine dehydrogenase, calcineurin, and endonucleases. Many of these enzymes can elicit generation of endogenous ROS (Rego A C, Oliveira C R. 2003. Mitochondrial dysfunction and reactive oxygen species in excitotoxicity and apoptosis: implications for the pathogenesis of neurodegenerative diseases. Neurochem Res 28: 1563-1574.). Moreover, an increase in mitochondrial $Ca^{2+}$ itself can also promote ROS generation (Kowaltowski A J, Castilho R F, Vercesi A E. 1995. $Ca^{2+}$-induced mitochondrial membrane permeabilization: role of coenzyme Q redox state. Am J Physiol 269: C141-147.), and intracellular $Ca^{2+}$ overload associated with excitotoxicity can induce both apoptosis and necrosis (Ankarcrona M, Dypbukt J M, Bonfoco E, Zhivotovsky B, Orrenius S, Lipton S A, Nicotera P. 1995. Glutamate-induced neuronal death: a succession of necrosis or apoptosis depending on mitochondrial function. Neuron 15: 961-973.). Therefore, elevation of intracellular $Ca^{2+}$ and increased ROS production are the major causes of neuronal death in excitotoxicity.

The potential for the consumption of tea or tea polyphenols to prevent or ameliorate chronic disease is becoming the subject of considerable scientific investigation. Although a number of mechanisms have been proposed to explain the beneficial effects of tea in different models of chronic disease, the radical scavenging and antioxidant properties of tea polyphenols are frequently cited as important contributors (Liang Y C, Lin-Shiau S Y, Chen C F, Lin J K. 1997. Suppression of extracellular signals and cell proliferation through EGF receptor binding by (−)-epigallocatechin gallate in human A431 epidermoid carcinoma cells. J Cell Biochem 67: 55-65.; Lin Y L, Lin J K. 1997. (−)-Epigallocatechin-3-gallate blocks the induction of nitric oxide synthase by downregulating lipopolysaccharide-induced activity of transcription factor nuclear factor-kappaB. Mol Pharmacol 52: 465-472.). Evidence supporting an antioxidant function for tea polyphenols is mainly derived from assays of their antioxidant activity in vitro. Recently, the in vivo evidence that tea polyphenols are acting directly or indirectly as antioxidants has been progressively expanded (Umemura T, Kai S, Hasegawa R, Kanki K, Kitamura Y, Nishikawa A, Hirose M. 2003. Prevention of dual promoting effects of pentachlorophenol, an environmental pollutant, on diethylnitrosamine-induced hepato- and cholangiocarcinogenesis in mice by green tea infusion. Carcinogenesis 24: 1105-1109.). In this aspect, animal studies can offer a unique opportunity to assess the contribution of the antioxidant properties of tea polyphenols to the physiological effects of tea administration in different models of oxidative stress (Frei B, Higdon J V. 2003. Antioxidant activity of tea polyphenols in vivo: evidence from animal studies. J Nutr 133: 3275S-3284S.).

Both treatment with memantine and combined treatment with memantine and tea polyphenol could significantly attenuate the decreased MTT activity. Data are represented as means±SEMs (P<0.01 compared with nonstriatal area; #P<0.05 compared with striatum of control group); S, sham operation group; C, control group; M, memantine group; TP, tea polyphenol group; and TP+M, tea polyphenol plus memantine group.

Figure 6:
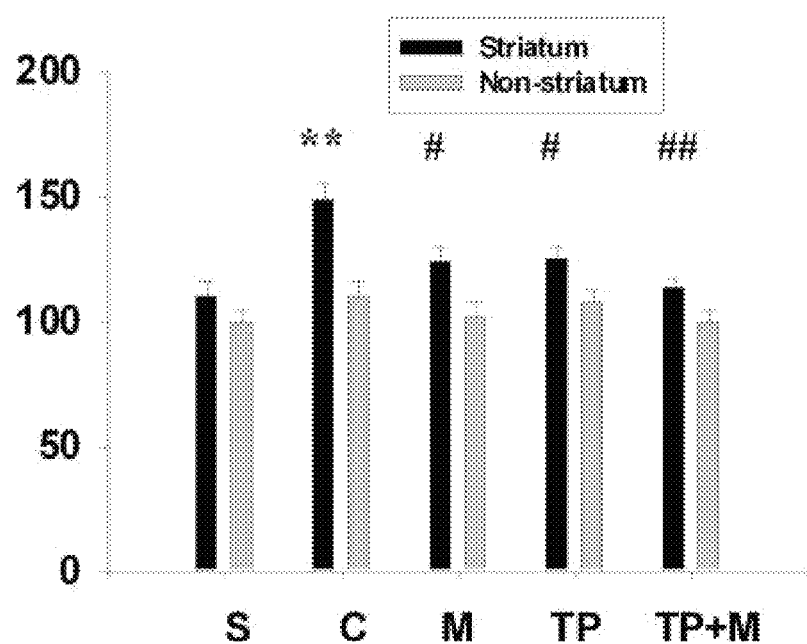

FIG. 6 shows determination of intrasynaptosomal $Ca^{2+}$ concentration in striatal and nonstriatal areas of mice 4 hr after excitotoxic injury. In the control group, excitotoxic injury caused a significant increase in intrasynaptosomal $Ca^{2+}$ concentration in the striatum. Treatment with memantine and tea polyphenol alone caused significantly attenuation of the increased intrasynaptosomal $Ca^{2+}$ concentration. Combined treatment with memantine and tea polyphenol caused further reduction in the increased intrasynaptosomal $Ca^{2+}$ concentration. Data are represented as means±SEMs (P<0.01 compared with nonstriatal area; #P<0.05 compared with striatum of control group); S, sham operation group; C, control group; M, memantine group; TP, tea polyphenol group; TP+M, tea polyphenol plus memantine group.

Figure 7:
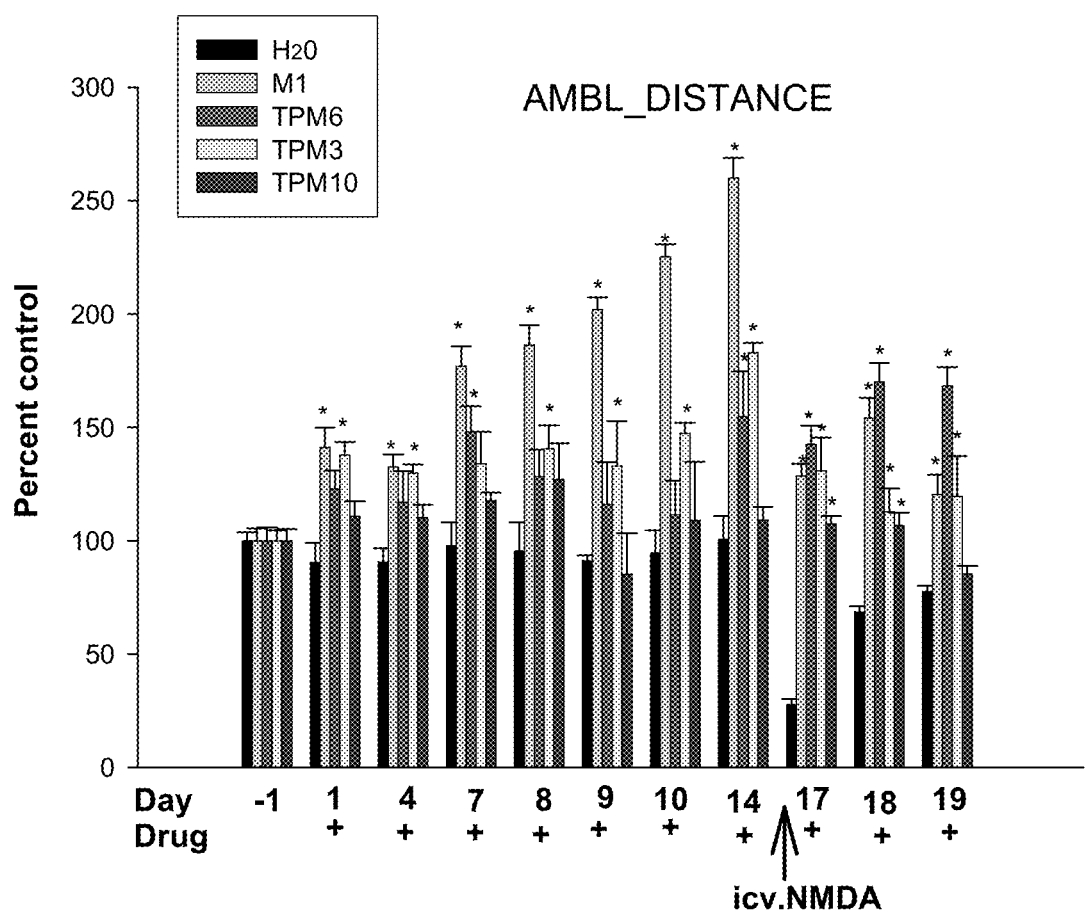

FIG. 7 shows the effects of drug pretreatments on NMDA-decreased locomotor activities of mice. Data are presented as mean±S.E. P<0.05. M1: memantine alone. TPM6, TPM3, and TPM10: tea polyphenol combined with memantine with dose ratio of 6, 3, and 10, respectively. icv. NMDA is the intracerebral injection of NMDA. AMBL_DISTANCE is ambulation distance.

Figure 8:
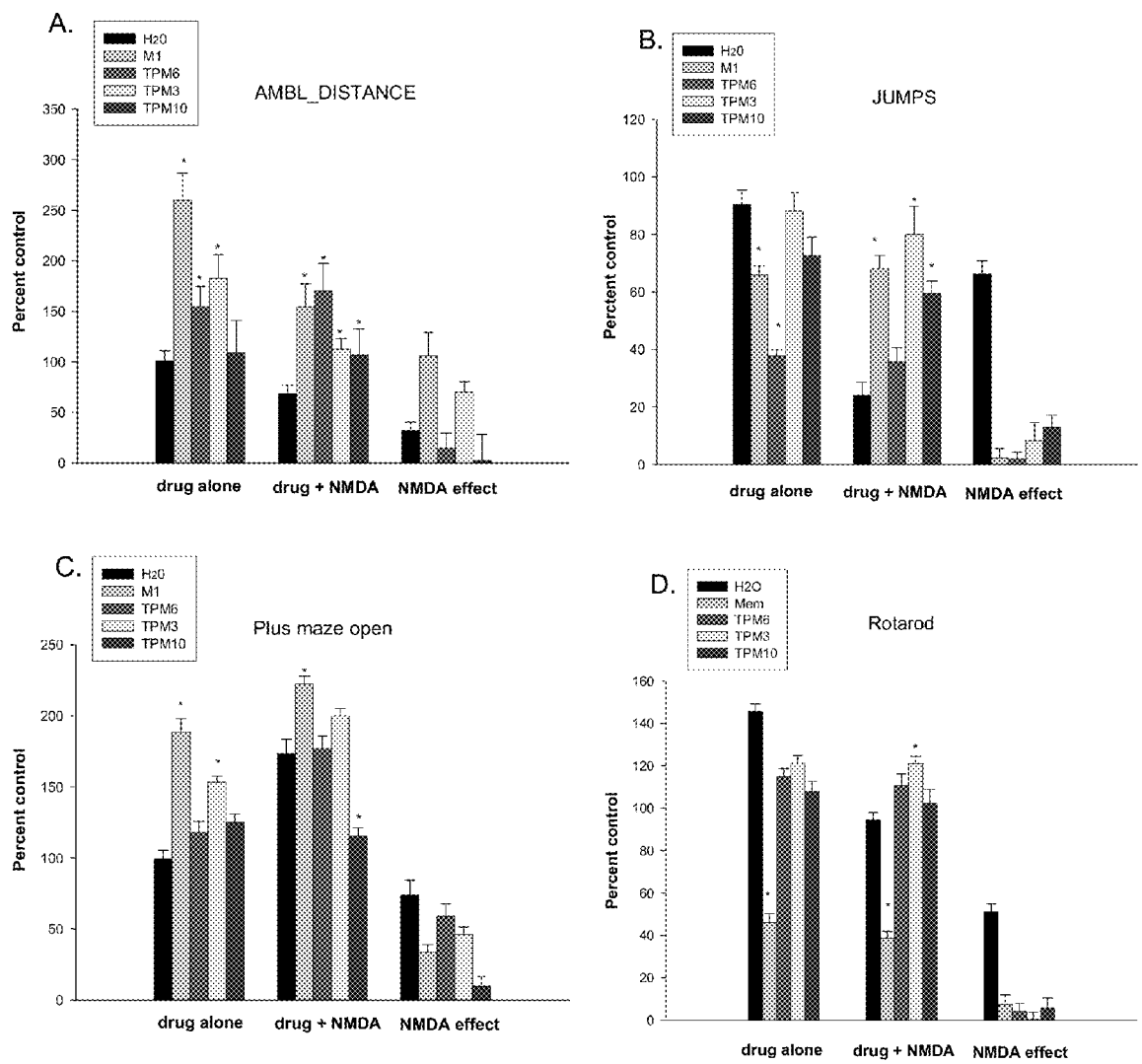

FIG. 8 shows the change of neurobehavioral activities after drug pretreatment and their influences on NMDA-induced neurotoxicities Data are presented as mean±S.E. P<0.05. M1/Mem: memantine alone. TPM6, TPM3, and TPM10: tea polyphenol combined with memantine with dose ratio of 6, 3, and 10, respectively. AMBL_DISTANCE is ambulation distance.

Figure 9:
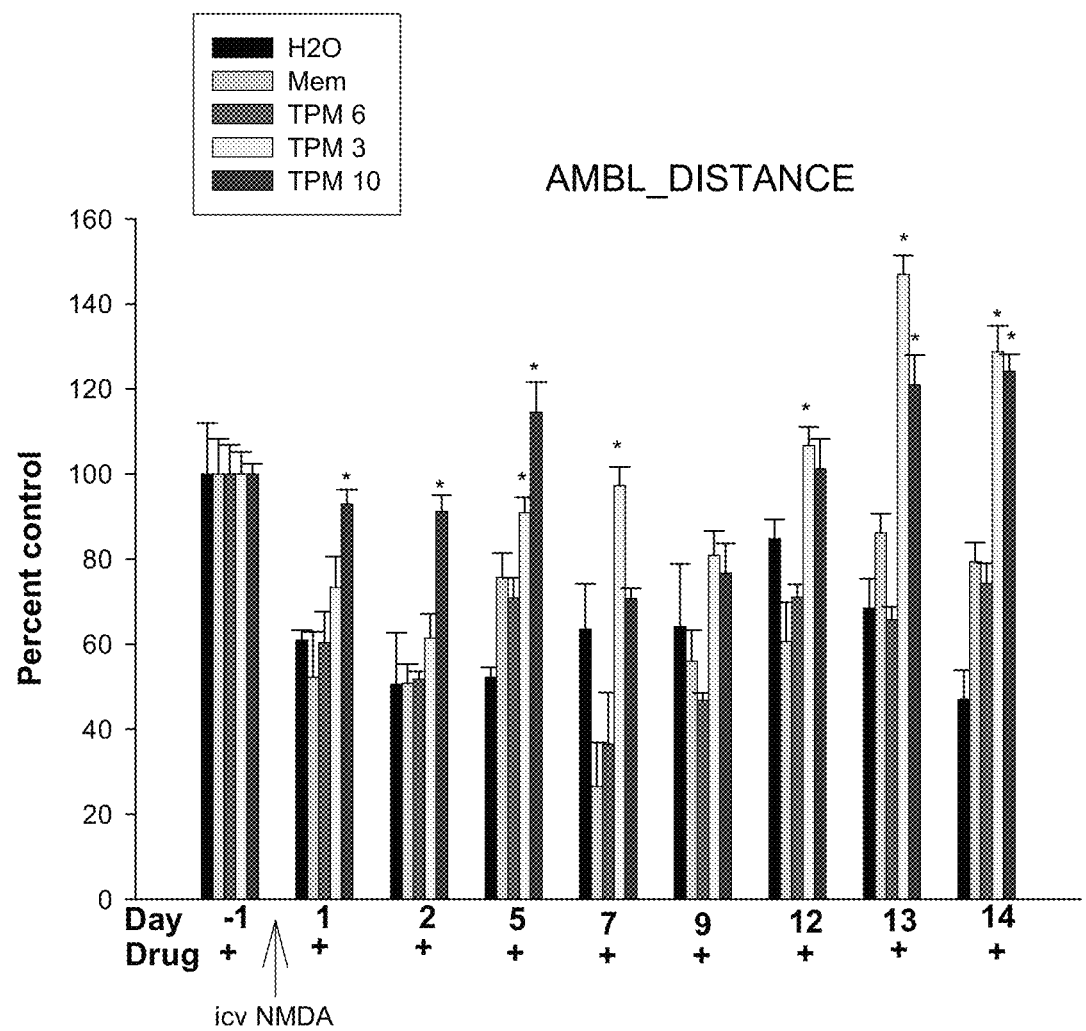

FIG. 9 shows the effects of drug treatments on NMDA-decreased locomotor activities of mice. Data are presented as mean±S.E. P<0.05. Mem: memantine alone. TPM6, TPM3, and TPM10: tea polyphenol combined with memantine with dose ratio of 6, 3, and 10, respectively. icv. NMDA is the intracerebral injection of NMDA. AMBL_DISTANCE is ambulation distance.

Figure 10:
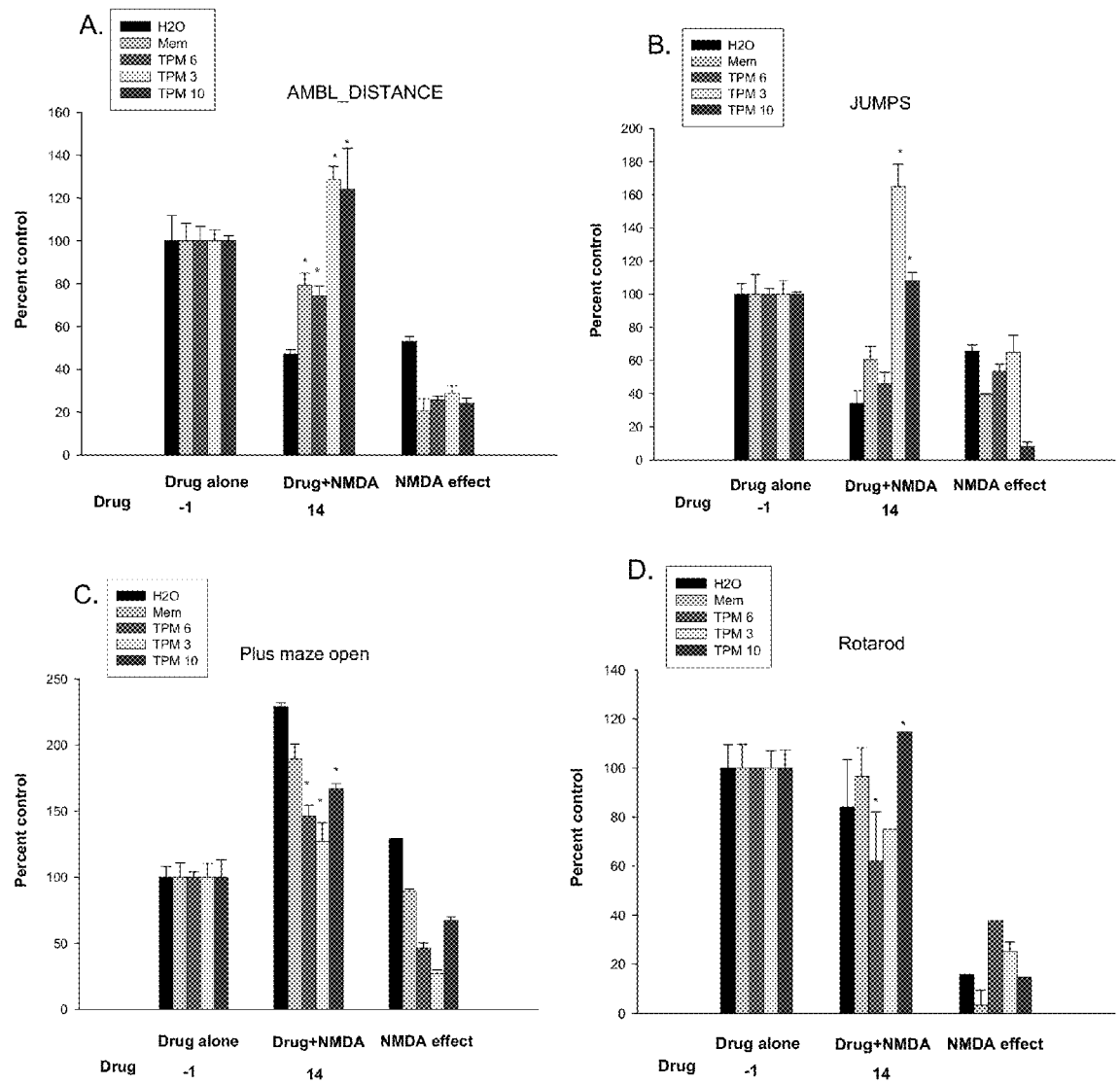

FIG. 10 shows the prolonged drug treatments on neurobehavioral activities following NMDA administration to mice. Data are presented as mean±S.E. P<0.05. Mem: memantine alone. TPM6, TPM3, and TPM10: tea polyphenol combined with memantine with dose ratio of 6, 3, and 10, respectively. AMBL_DISTANCE is ambulation distance.

Figure 11:
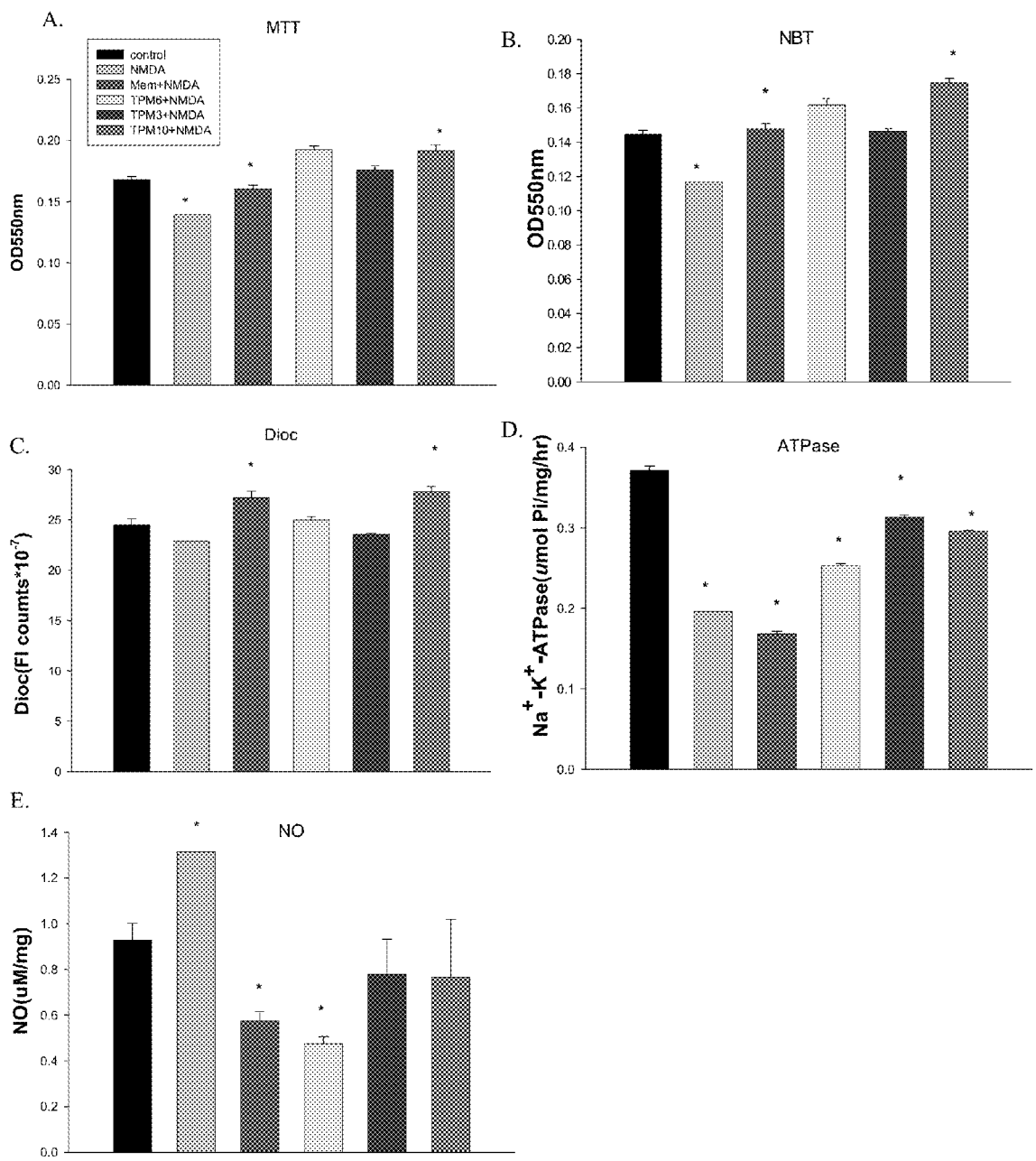

FIG. 11 shows the neurochemical changes of brain synaptosomes after drug treatments of the mice administered with NMDA. Data are presented as mean±S.E. P<0.05. Mem: memantine alone. TPM6, TPM3, and TPM10: tea polyphenol combined with memantine with dose ratio of 6, 3, and 10, respectively.

SUMMARY OF THE INVENTION

The present invention discloses a method for preventing or treating a subject suffering from a disease or condition associated with excitotoxicity, comprising administering to the subject a therapeutically effective amount of a composition comprising N-methyl-D-aspartate (NMDA) receptor antagonist and tea polyphenol in combination, wherein the ratio of tea polyphenol and NMDA receptor antagonist is from 3:1 to 10:1, whereby the composition provides synergistic neuroprotective effect to the subject.

DETAILED DESCRIPTION OF THE INVENTION

This invention demonstrated that intrastriatal injection of NMDA caused impairment in locomotor activity, increased production of synaptosomal ROS, and a decrease in all $Na^+$, $K^+$-ATPase and $Mg^{2+}$-ATPase activity, mitochondrial membrane potential ($\Delta\Psi m$), and mitochondrial reductase activity in mice. Treatment with tea polyphenol could significantly decrease the increased synaptosomal ROS production, and attenuate the decreased $Na^+$, $K^+$-ATPase and $Mg^{2+}$-ATPase activity. By contrast, treatment with memantine could significantly attenuate the decreased mitochondrial membrane potential ($\Delta\Psi m$) and mitochondrial reductase activity. However, neither memantine nor tea polyphenol alone could significantly improve the impaired locomotor activity after excitotoxic injury. A promising regimen through combination of memantine and tea polyphenol significantly improved locomotor activity, decreased synaptosomal ROS production, and attenuated all the decreases in $Na^+$, $K^+$-ATPase and $Mg^{2+}$-ATPase activity, mitochondrial membrane potential ($\Delta\Psi m$), and mitochondrial reductase activity in mouse excitotoxic injury. Therefore, it is suggested that memantine, an NMDA receptor antagonist, combined with tea polyphenol, an antioxidant, is more effective in neuroprotection than is either alone in mouse excitotoxic injury.

Excitotoxicity is an attractive target for neuroprotective efforts because it is involved in the pathophysiology of a wide variety of acute and chronic neurological disorders. Trying to devise strategies for combating excitotoxicity is still a challenging task because the same processes that in excess lead to excitotoxic cell death are absolutely critical for normal neuronal function at lower levels. To be clinically acceptable, an NMDA receptor antagonist must block excessive activation of NMDA receptors while leaving normal function relatively intact in order to avoid side effects. The term open-channel blocker of the NMDA receptor means that the drug enters the receptor-associated ion channel only when it is open. Importantly, this type of drug will be most effective in the face of excessive (pathological) activity. This mechanism of inhibition, whose action depends on prior activation of the receptor by the agonist, is defined as uncompetitive antagonism. For therapeutic intervention during excessive NMDA receptor activation, open-channel block is a very appealing strategy because the action of the blockade requires prior activation of the receptors. This property can lead to a higher degree of channel blockade in the presence of excessive levels of glutamate and only little blockade at relatively lower levels to maintain physiological neurotransmission (Chen H S, Lipton S A. 2006. The chemical biology of clinically tolerated NMDA receptor antagonists. J Neurochem 97: 1611-1626.). Memantine is an ideal NMDA receptor antagonist through its action as a low-affinity, uncompetitive open-channel blocker.

In the present invention, treatment with memantine could significantly attenuate the decreased mitochondrial membrane potential ($\Delta\Psi m$) and mitochondrial reductase activity in mouse excitotoxic injury. Memantine does not have any significant effects on increased synaptosomal ROS production and decreased $Na^+$, $K^+$-ATPase and $Mg^{2+}$-ATPase activity. Therefore, treatment with memantine alone caused nonsignificant improvement in the impaired locomotor activity. Energy depletion is among the frequent initiating conditions leading to excitotoxicity, and mitochondrial dysfunction is believed to be one of the most generalized causes favoring the development of neurodegenerative diseases. Memantine has been tested in animals against primary insults dependent on mitochondrial impairment and energy depletion and has provided protection from inhibition of mitochondrial function (Rego A C, Oliveira C R. 2003. Mitochondrial dysfunction and reactive oxygen species in excitotoxicity and apoptosis: implications for the pathogenesis of neurodegenerative diseases. Neurochem Res 28: 1563-1574.). Therefore, the neuroprotective effect of memantine in excitotoxic injury depends on amelioration of mitochondrial dysfunction, which was well demonstrated in our experiment. However, memantine lacks the ability to scavenge the excessive production of ROS and its associated toxic outcomes. In an excitotoxic injury model with an acutely high concentration of NMDA, as in our experiment or in acute stroke, memantine alone is not adequate for significant neuroprotection.

It is well documented that mitochondrial dysfunction associated with the loss of $Ca^{2+}$ homeostasis and enhanced cellular oxidative stress has long been recognized to play a major role in cell damage associated with excitotoxicity. $Na^+$, $K^+$-ATPase is known to be highly susceptible to free-radical damage and lipid peroxidation because of its plasmalemmal embedding and its phospholipid requirement for maintenance of activity (Ildan F, Polat S, Gocer A I, Oner A, Isbir T, Mete U O, Kaya M, Karadayi A. 1996. The effects of the pretreatment of intravenous high dose methylprednisolone on $Na^+$—$K^+$/$Mg^{2+}$-ATPase and lipid peroxidation and early ultrastructural findings following middle cerebral artery occlusion in the rat. Acta Neurochir (Wien) 138: 338-345.). $Mg^{2+}$-ATPase is also vulnerable to damage by reactive oxygen species. It is therefore proposed that failure of memantine to attenuate the decrease in $Na^+$, $K^+$-ATPase and $Mg^{2+}$-ATPase activity is a result of its inability to scavenge the increased production of ROS.

Treatment with tea polyphenol can significantly decrease the increased production of synaptosomal ROS and attenuate the decreased $Na^+$, $K^+$-ATPase and $Mg^{2+}$-ATPase activity, and unlike memantine, tea polyphenol has little effect on attenuation of decreased mitochondrial membrane potential ($\Delta\Psi m$) and mitochondrial reductase activity. Thus, treatment with tea polyphenol alone also failed to significantly improve impaired locomotor activity induced by excitotoxic injury. Yazawa et al. (Yazawa K, Kihara T, Shen H, Shimmyo Y, Niidome T, Sugimoto H. 2006. Distinct mechanisms underlie distinct polyphenol-induced neuroprotection. FEBS Lett 580: 6623-6628.) showed that the possible mechanisms involved in polyphenol-induced neuroprotection include inhibition of protein kinase activity, reduction of glutamate-mediated $Ca^{2+}$ influx, inhibition of glutamate-induced caspase-3 activation, and reduction of glutamate-induced generation of ROS. Our results showed that treatment with tea polyphenol can reduce glutamate-induced ROS and attenuate decreased $Na^+$, $K^+$-ATPase and $Mg^{2+}$-ATPase activity. These results further support the neuroprotective role of tea polyphenol in excitotoxicity. However, because of a lack of protection in mitochondrial dysfunction, treatment with tea polyphenol alone failed to improve impaired locomotor activity in our excitotoxic model.

This invention disclosed a novel regimen to use, the combined treatment of memantine and tea polyphenol, in excitotoxic injury. The results showed significant protection against excitotoxic injury with combined treatment with memantine and tea polyphenol. The neuroprotective effects included reduction in increased synaptosomal ROS and $Ca^{2+}$ concentration and attenuation of decreased $Na^+$, $K^+$-ATPase and $Mg^{2+}$-ATPase activity, mitochondrial membrane potential ($\Delta\Psi m$), and mitochondrial reductase activity. Moreover, impairment in locomotor activity was also significantly improved. Therefore, combined treatment with memantine and tea polyphenol is more effective in neuroprotection than memantine or tea polyphenol alone in mouse excitotoxic injury.

Combined treatment with memantine and tea polyphenol is more effective in neuroprotection than memantine or tea polyphenol alone in mouse excitotoxic injury. Further experiments are needed to explore the efficacy of such a novel regimen in the treatment of neurodegenerative and other neurological diseases.

Accordingly, the present invention discloses a composition, comprising N-methyl-D-aspartate (NMDA) receptor antagonist and tea polyphenol in combination and the ratio of tea polyphenol and NMDA receptor antagonist is from 3:1 to 10:1. In a preferred embodiment of the composition, NMDA receptor antagonist is memantine or a pharmaceutically acceptable analog and tea polyphenol consists of polyphenolic antioxidant metabolites. In another preferred embodiment of the composition, the ratio of tea polyphenol and NMDA receptor antagonist is 10:1

The present invention also discloses a method for preventing or treating a subject suffering from a disease or condition associated with excitotoxicity resulted from NMDA receptor over-activation, said method comprising administering to the subject a therapeutically effective amount of the composition comprising N-methyl-D-aspartate (NMDA) receptor antagonist and tea polyphenol in combination, wherein the ratio of tea polyphenol and NMDA receptor antagonist is from 3:1 to 10:1, whereby the composition provides synergistic neuroprotective effect to the subject. Said preventing or treating is made by attenuating mitochondria dysfunction associated with loss of $Ca^{2+}$ homeostasis and enhanced cellular oxidative stress. In a preferred embodiment of the method, the disease or condition associated with excitotoxicity resulted from NMDA receptor over-activation is neurodegenerative disease or condition.

In addition, the neurodegenerative disease or condition is brain trauma, brain ischemia, epilepsy, or Alzheimer's diseases. And the subject to be administered is human.

The present invention further discloses a method for providing synergistic neuroprotective effect, said method comprising administrating to the subject a therapeutically effective amount of the composition of the present invention. The synergistic neuroprotective effect is made by attenuating mitochondria dysfunction associated with loss of $Ca^{2+}$ homeostasis and enhanced cellular oxidative stress. And the subject to be administered is human.

The term "synergistic neuroprotective effect" is not limited but to make through attenuating mitochondria dysfunction associated with loss of $Ca^{2+}$ homeostasis and enhanced cellular oxidative stress.

EXAMPLES

Example 1

Mice

The experiment protocols were approved by the Hospital Animal Research Committee of National Taiwan University Hospital. Adult male ICR mice weighing 20-25 g were used in this example.

Treatment of Mice

Memantine hydrochloride (>98.5% white crystalline powder) was supplied by Lotus Pharmaceutical Co., Ltd. (Taipei, Taiwan). Tea polyphenols were isolated from Longjing green tea with the following composition: epigallocatechin, 14.69%; catechin, 1.13%; epigallocatechin-3-gallate, 41.34%; epicatechin, 5.47%; gallocatechin-3-gallate, 5.16%; epicatechin-3 gallate, 12.54%; coffein, 0.95%; and other catechin derivatives, 18% (Yeh C W, Chen W J, Chiang C T, Lin-Shiau S Y, Lin J K. 2003. Suppression of fatty acid synthase in MCF-7 breast cancer cells by tea and tea polyphenols: a possible mechanism for their hypolipidemic effects. Pharmacogenomics J 3: 267-276.). Memantine (10 mg/kg/day), tea polyphenol (60 mg/kg/day), or a combination (memantine 5 mg/kg/day plus tea polyphenol 30 mg/kg/day) was dissolved in distilled water and administered by oral gavage for 2 consecutive days before causing excitotoxic injury. The experimental design had 5 groups: the sham operation group, the control group, the memantine group, the tea polyphenol group, and the tea polyphenol plus memantine group.

Excitotoxic Injury

Weight and rectal temperature of each mouse were recorded before the surgical procedure. Anesthesia was induced with 5% chloral hydrate (400 mg/kg). Each mouse was mounted on a stereotactic frame, and 0.3 L of NMDA (335 mM, pH, 7.2) prepared in phosphate-buffered saline was injected into the left striatum (stereotactic coordinates: PA 0.5 mm, lateral 3.0 mm from bregma, and ventral 4 mm relative to dura) over a 2-min period; the needle was left in situ for an additional 5 min to prevent backflow. All five groups of mice received the same procedure except that the same amount of normal saline was injected in the sham operation group. After injections, mice were placed in a humidified, thermoregulated chamber maintained at 31° C. and were returned to their cages after full recovery from anesthesia. Throughout the experimental procedure, mouse rectal temperature was monitored and maintained at 37.0° C.±0.5° C.

Preparation of Synaptosomes

Twenty-four hours after excitotoxic injury, mice were sacrificed by rapid decapitation under anesthesia. The lesioned (left) hemisphere was dissected into striatal and nonstriatal areas. The contralateral hemisphere was then dissected into the corresponding parts. Synaptosomes were prepared essentially as described previously (Andersen J M, Myhre O, Fonnum F. 2003. Discussion of the role of the extracellular signal-regulated kinase-phospholipase A2 pathway in production of reactive oxygen species in Alzheimer's disease. Neurochem Res 28: 319-326.). Briefly, different regions of the brain were removed and placed on ice. Specimens with the same areas and treatment conditions were pooled (n=2) and subjected to homogenization on ice in 10 volumes of 0.32M sucrose. Homogenates were centrifuged at 4° C. for 10 min at 600 g. The supernatant was then diluted 1:1 with 1.3M sucrose to obtain a suspension with a final sucrose concentration of 0.8M. This suspension was subjected to centrifugation at 20,000 g for 30 min at 4° C., yielding a myelin-rich supernatant and a pellet (P2) consisting of synaptosomes free of myelin. The supernatant was discarded, and the pellet was resuspended in 0.32M sucrose buffer (pH 7.4). Synaptosomes were held on ice, usually for 15-20 min, until experiments were performed. The concentration of synaptosomes used for the experiments was corrected as milligrams of protein.

Statistical Analysis

Statistical comparisons between study groups were performed using analysis of variance followed by Dunnett's test. P values less than 0.05 were considered biologically significant.

Locomotor Activity Test

All experiment animals received a locomotor activity test 1 day before and 1 day after excitotoxic injury.

Result:

Locomotor Activity was Impaired after Excitotoxic Injury and Attenuated by Combined Treatment with Memantine and Tea Polyphenol.

Figure 1:
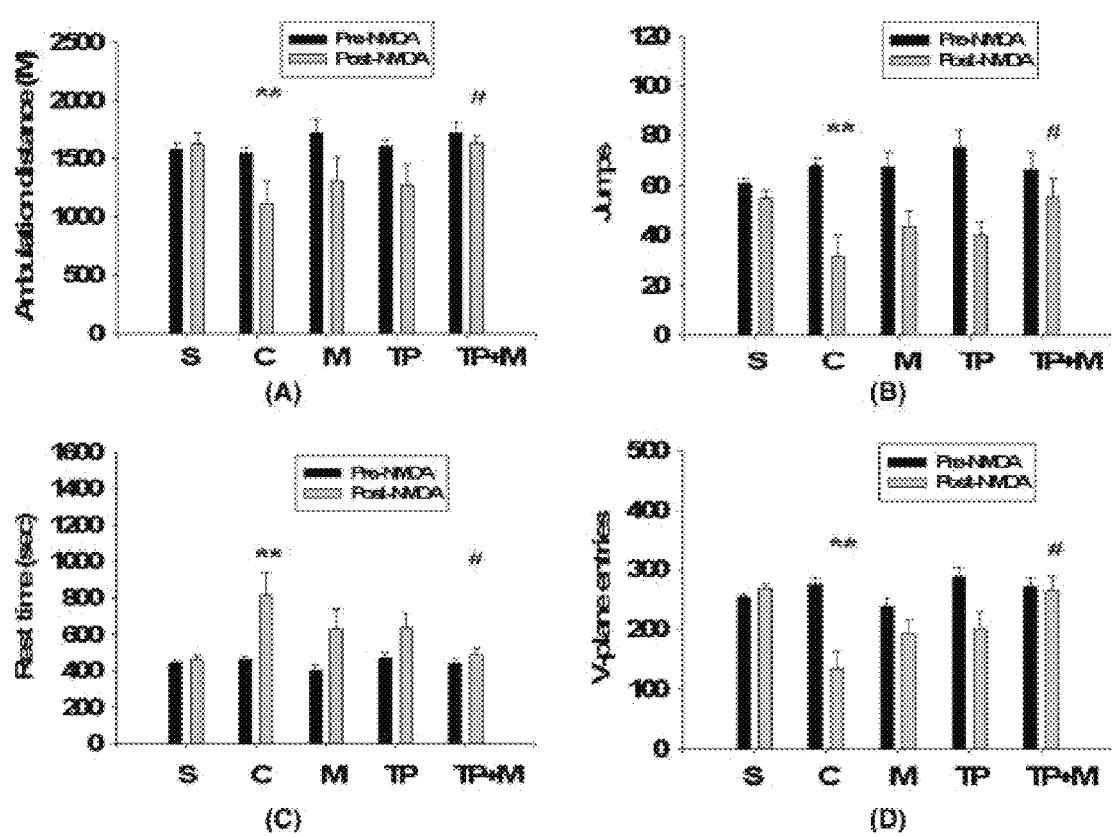
FIG. 1 shows locomotor activities of mice assayed before and after excitotoxic injury. In control group, significant impairment in locomotor activity was noted after excitotoxic injury. Combined treatment with memantine and tea polyphenol could significantly improve the impaired locomotor activity. The improved locomotor activity included: (A) an increase in ambulation distance; (B) an increase in jumps; (C) a decrease in rest time; and (D) an increase in vertical plane entries. Data are presented as means±SEMs ($P<0.01$ compared with preoperative tests; $\#P<0.05$ compared with postoperative control group); S, sham operation group; C, control group; M, memantine group; TP, tea polyphenol group; and TP+M, tea polyphenol plus memantine group.

The administration of NMDA in mouse striatum caused significant impairment of locomotor activity. Locomotor activity tests administered to the experimental mice were recorded 24 hr before and after excitotoxic injury. In the control group, a significant decrease was noted in ambulation distance, jump, and vertical plane entry after excitotoxic injury (n=8, $P<0.01$; FIG. 1). An increase in rest time was also noted. Treatment with memantine or tea polyphenol alone caused substantial but nonsignificant improvement in the impaired locomotor activity. Combined treatment with memantine and tea polyphenol could significantly protect mice from impairment of locomotor activity after excitotoxic injury (n=8, $P<0.05$; FIG. 1).

Measurements of $Na^+$, $K^+$-ATPase Activity

ATPase activity was determined by measuring the amount of inorganic phosphate (Pi) released from the substrate ATP according to a previously described colorimetric method. The method permitted the quantification of $Na^+$, $K^+$-ATPase and $Mg^{2+}$-ATPase activity in the same sample. Briefly, ATPase reactions were initiated in a mixture containing NaCl (354 mM), KCl (14.4 mM), $MgCl_2$ (3.6 mM), $NaHCO_3$ (37.5 mM), ethyleneglycol bis(amino-ethylether) tetraacetate (1.5 mM), glucose (33.3 mM), and ATP (9 mM) and in the absence or presence of ouabain (1 mM). Synaptosomes prepared from different areas (striatum and nonstriatum) of the same brain were incubated at 37° C.±0.5° C. for 30 min in the reaction mixture. Reactions were terminated by the addition of 150 L of a solution containing ammonium molybdate (1.05%), malachite green hydrochloride (0.034%), and Triton-X (0.6%). To stabilize the color reaction, 10 L of a sodium citrate solution (34%) was added, and the assay solution was held at room temperature for 20 min. Optical density at 630 nm was determined by an ELISA reader (Dynatech MR-7000). The absorbance values obtained were converted to activity values by linear regression using a standard curve for sodium monobasic phosphate included in the assay at various concentrations. Pi released (in mmol/L) was taken to represent the concentration of inorganic phosphate released by the enzymatic hydrolysis of ATP. $Na^+$, $K^+$-specific ATPase activity was determined by subtracting ouabain-insensitive $Mg^{2+}$-ATPase activity from total $Na^+$, $K^+$- and $Mg^{2+}$-ATPase activity (Cheng P W, Liu S H, Hsu C J, Lin-Shiau S Y. 2005. Correlation of increased activities of $Na^+$, $K^+$-ATPase and $Ca^{2+}$-ATPase with the reversal of cisplatin ototoxicity induced by D-methionine in guinea pigs. Hear Res 205: 102-109.). Protein concentration was determined colorimetrically with a commercial bicinchoninic acid kit (Pierce, Rockford, Ill.).

Result:

$Na^+$, $K^+$-ATPase and $Mg^{2+}$-ATPase Activity Decreased after Excitotoxic Injury and Was Preserved by Treatment with Tea Polyphenol or Combined Treatment of Memantine and Tea Polyphenol.

Figure 2:
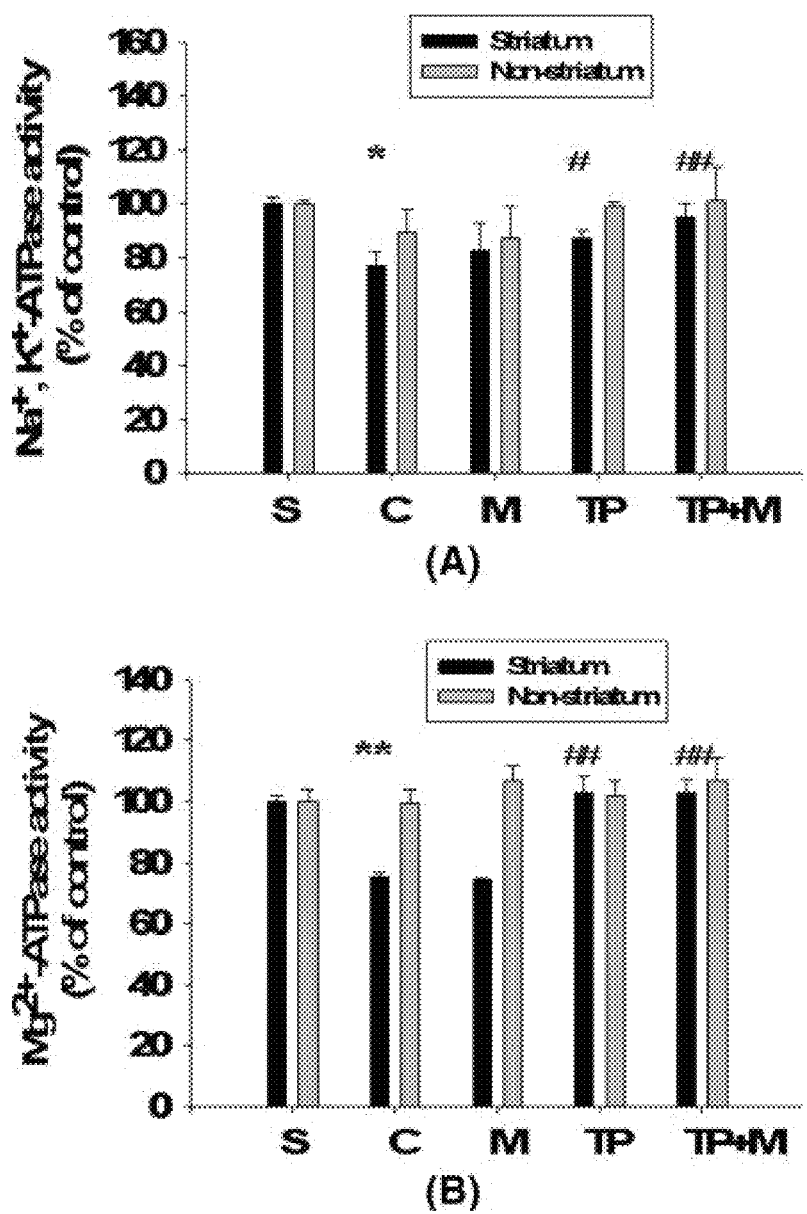
FIG. 2 shows measurement of $Na^+$, $K^+$-ATPase and $Mg^{2+}$-ATPase activity in striatal and nonstriatal areas of mice. In the control group, excitotoxic injury for 24 hr caused a significant decrease in $Na^+$, $K^+$-ATPase and $Mg^{2+}$-ATPase activity in the striatum. Treatment with tea polyphenol and combined treatment with memantine and tea polyphenol could significantly attenuate the decreased $Na^+$, $K^+$-ATPase (A) and $Mg^{2+}$-ATPase (B) activity. Data are represented as means±SEMs ($P<0.05$, $P<0.01$ compared with nonstriatal area; $\#P<0.05$, $\#\#P<0.01$ compared with striatum of control group); S, sham operation group; C, control group; M, memantine group; TP, tea polyphenol group; and TP+M, tea polyphenol plus memantine group.

Twenty-four hours after excitotoxic injury, the brain was dissected, and synaptosomes were prepared. In the control group, synaptosomal $Na^+$, $K^+$-ATPase and $Mg^{2+}$-ATPase activity was significantly decreased in striatum after excitotoxic injury (FIG. 2). Treatment with memantine alone only minimally attenuated the decreased $Na^+$, $K^+$-ATPase and $Mg^{2+}$-ATPase activity. Treatment with tea polyphenol or combined treatment with memantine and tea polyphenol significantly attenuated the decrease in striatal $Na^+$, $K^+$-ATPase activity (treatment with tea polyphenol and combined treatment with memantine and tea polyphenol vs. control group: 87.62%±2.36% and 92.35%±8.22% vs. 77.28%±5.29%, P<0.05 and P<0.01 respectively; FIG. 2A) and $Mg^{2+}$-ATPase activity (treatment with tea polyphenol and combined treatment with memantine and tea polyphenol vs. control group: 95.32%±5.25% and 98.03%±5.75% vs. 75.26%±3.84%, P<0.01; FIG. 2B) from excitotoxic injury.

Measurement of Reactive Oxygen Species Formation

Dichlorofluorescein-diacetate (DCFH-DA), a nonfluorescent cell-permeable compound, diffuses passively across cell membranes. Following cellular uptake, the acetate groups are cleaved by intracellular esterases, yielding 2,7-dichlorofluorescin (DCFH). DCFH is oxidized by hydroxyl radicals, peroxynitrite, or $H_2O_2$ (in the presence of peroxidases) to a fluorescent compound, 2,7-dichlorofluorescein (DCF; Myhre O, Andersen J M, Aarnes H, Fonnum F. 2003. Evaluation of the probes 2,7-dichlorofluorescin diacetate, luminol, and lucigenin as indicators of reactive species formation. Biochem Pharmacol 65: 1575-1582.). Production of the latter was therefore used as an index of reactive oxygen species formation. Synaptosomes were diluted 1:40 in 0.32M sucrose buffer prior to loading with 10 M DCFH-DA for 15 min at 37° C. Working solutions were prepared daily by diluting stock solutions in 0.32M sucrose buffer to 1.67× the desired final concentration; 150 L of this working solution was then placed in wells of 96-well microplates. The reaction was initiated by the addition of 100 L of the synaptosomal solution to each well (final reaction volume of 250 L). Plates were incubated with shaking at 37° C. for 30 min before measurement of fluorescence using a Microplate Fluorometer (Labsystems, Helsinki, Finland) with an excitation wavelength of 488 nm, an emission wavelength of 525 nm, and a band width of 5 nm. Blank values were obtained from wells containing buffer and synaptosomes that had not been loaded with DCFH-DA. Synaptosomal protein concentration was determined with Pierce BCA reagents according to instructions provided. DCF fluorescence values were corrected for protein values and autofluorescence of the samples according to the formula Fco= (Fsa−Fbl)/synaptosomal protein, where Fco was the corrected fluorescence value, Fsa was the observed fluorescence of the sample, and Fbl was the observed fluorescence of the blank.

Figure 3:
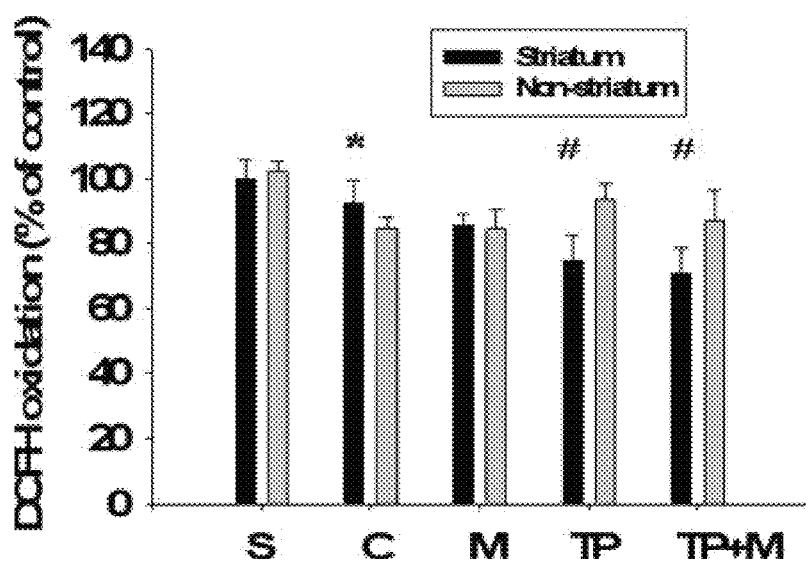
FIG. 3 shows measurement of production of synaptosomal reactive oxygen species in striatal and nonstriatal areas of mice 24 hr after excitotoxic injury. In the control group, excitotoxic injury caused a significant increase in synaptosomal reactive oxygen species production in striatum. Treatment with tea polyphenol and combined treatment with memantine and tea polyphenol could significantly decrease production of synaptosomal reactive oxygen species in striatum. Data are represented as means±SEMs ($P<0.05$ compared with nonstriatal area; $\#P<0.05$; $\#\#P<0.01$ compared with striatum of control group); S, sham operation group; C, control group; M, memantine group; TP, tea polyphenol group; and TP+M, tea polyphenol plus memantine group.

Result:

Increased Production of Reactive Oxygen Species after Excitotoxic Injury and Decreased Production by Treatment with Tea Polyphenol or Combined Treatment with Memantine and Tea Polyphenol In striatum, the synaptosomal production of reactive oxygen species was significantly increased after excitotoxic injury (n=8, P<0.05). Similar to ATPase, treatment with tea polyphenol alone or combined treatment with memantine and tea polyphenol significantly decreased the production of synaptosomal reactive oxygen species (treatment with tea polyphenol and combined treatment with memantine and tea polyphenol vs. control group: 74.57%±7.72% and 70.65%±7.97% vs. 92.83%±6.65%, P<0.05; FIG. 3).

Mitochondrial Membrane Potential

Mitochondrial membrane potential (ΔΨm) was measured using the fluorescent dye 3,3-diexyloxacarbocyanine iodide, DiOC6(3) (Chen Y C, Lin-Shiau S Y, Lin J K, 1998b. Involvement of reactive oxygen species and caspase 3 activation in arsenite-induced apoptosis. J Cell Physiol 177: 324-333.). Synaptosomes were prepared as described above and diluted 1:40 in Tris buffer, followed by the addition of DiOC6(3) to a final concentration of 1.5 M. After 20 min of incubation at 37° C., fluorescence was measured in a Microplate Fluorometer (Labsystems, Helsinki, Finland) with an excitation wavelength of 484 nm and an emission wavelength of 501 nm.

Figure 4:
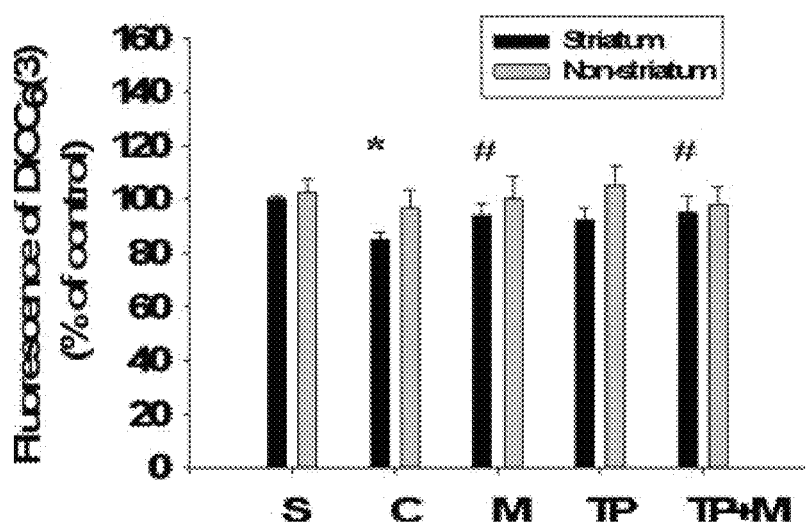
FIG. 4 shows detection of mitochondrial membrane potential ($\Delta\Psi m$) in striatal and nonstriatal areas of mice. In the control group, excitotoxic injury for 24 hr caused a significant decrease in mitochondrial membrane potential ($\Delta\Psi m$) in striatum. Treatment with memantine and combined treatment with memantine and tea polyphenol could significantly attenuate the decreased mitochondrial membrane potential ($\Delta\Psi m$). Data are represented as means±SEMs ($P<0.05$ compared with nonstriatal area; $\#P<0.05$ compared with striatum of control group); S, sham operation group; C, control group; M, memantine group; TP, tea polyphenol group; and TP+M, tea polyphenol plus memantine group.

Result:

Mitochondrial Membrane Potential (ΔΨm) Decreased after Excitotoxic Injury and was Preserved by Treatment with Memantine or Combined Treatment with Memantine and Tea Polyphenol The mitochondrial membrane potential (ΔΨm) was measured using DiOC6(3) 24 hr after excitotoxic injury (n=8, P<0.05). The mitochondrial membrane potential significantly decreased after excitotoxic injury. Treatment with memantine or combined treatment with memantine and tea polyphenol significantly attenuated the decrease in mitochondrial membrane potential (treatment with memantine and combined treatment with memantine and tea polyphenol vs. control group: 94.23%±4.19% and 97.34%±5.02% vs. 85.06%±2.58%, P<0.05; FIG. 4).

Assessment of Mitochondrial Metabolic Function

Mitochondrial metabolic function was assessed by the conversion of the dye methylthiazoletetrazolium (MTT) to purple formazan. This assay was based on the ability of mitochondrial succinate reductase to metabolize MTT to formazan; this reaction took place only in functionally intact mitochondria. P2 synaptosomes were prepared as described above. Working solutions (150 L) were added to microtubes, and 100 L of the synaptosome suspension and 25 L of a 5.0 mg/mL solution of MTT in 0.32M sucrose buffer were added to each tube. The samples were incubated for 120 min at 37° C. The purple formazan crystals were pelletized by centrifugation and the supernatant discarded. The pellets were dissolved in dimethyl sulfoxide and transferred to 96-well microplates. The formation of formazan was quantitated spectrophotometrically at 570 nm using a Microplate Reader.

Result:

Mitochondrial Reductase Activity Decreased after Excitotoxic Injury and was Attenuated by Treatment with Memantine or Combined Treatment with Memantine and Tea Polyphenol.

Figure 5:
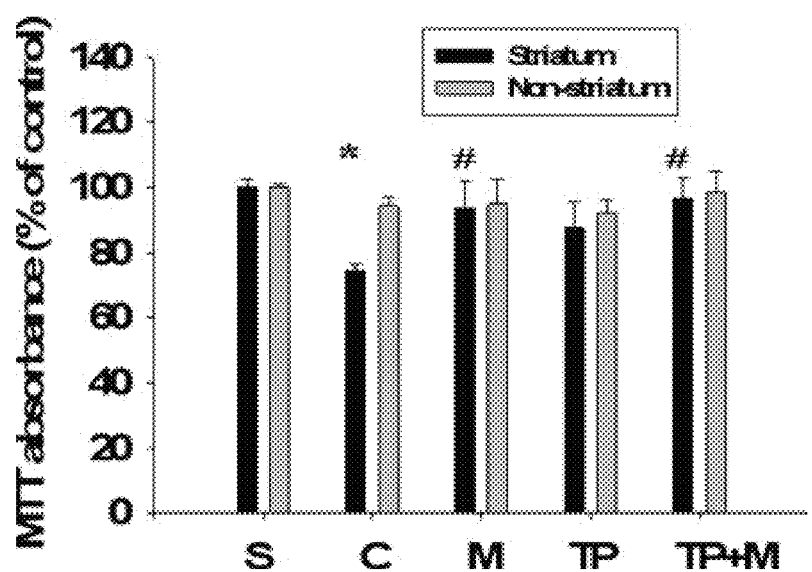
FIG. 5 shows determination of mitochondrial reductase (MTT) activity in striatal and nonstriatal areas of mice. In the control group, 24 hr after excitotoxic injury caused a significant decrease in mitochondrial reductase activity in striatum.

Mitochondrial reductase activity (MTT test) was measured 24 hr after excitotoxic injury. In the control group, the reductase activity decreased significantly after excitotoxic injury (n=8, P<0.01). Treatment with memantine or combined treatment with memantine and tea polyphenol significantly attenuated the decrease in reductase activity (treatment with memantine and combined treatment with memantine and tea polyphenol vs. control group: 93.53%±8.53% and 96.65%±6.42% vs. 74.52%±4.86%, P<0.05; FIG. 5).

Measurement of Intrasynaptosomal $Ca^{2+}$ Concentration

Intrasynaptosomal $Ca^{2+}$ concentration $[Ca^{2+}]i$ was determined with the calcium-sensitive fluorochrome fluo-3-acetoxymethyl (Fluo-3/AM) in the presence of acetoxymethyl ester. First, 100 L of P2 synaptosomes was prepared as described above, and 2.5 mM Fluo-3/AM (Sigma, St. Louis, Mo.) was added to each well (final reaction volume of 250 L) and incubated at 37° C. for 30 min. Fluorescence was measured in a Microplate Fluorometer (Labsystems, Helsinki, Finland) with an excitation wavelength of 490 nm and an emission wavelength of 526 nm.

Result:

Intrasynaptosomal $Ca^{2+}$ Concentration Increased after Excitotoxic Injury and was Attenuated by Treatment with Memantine and Tea Polyphenol Alone or in Combination.

The intrasynaptosomal $Ca^{2+}$ concentration, $[Ca^{2+}]i$, was measured 4 hr after excitotoxic injury. In the control group, the $[Ca^{2+}]i$ increased significantly after excitotoxic injury (n=10, P<0.01). Treatment with memantine and tea polyphenol alone significantly attenuated the increased $[Ca^{2+}]i$ (treatment with memantine and tea polyphenol vs. control group: 123.04%±6.70% and 122.97%±6.10% vs. 145.62%±7.16%, P<0.05). Combined treatment with memantine and tea polyphenol further reduced the increased $[Ca^{2+}]i$ (combined treatment with memantine and tea polyphenol vs. control group: 111.74%±3.82% vs. 145.62%±7.16%, P<0.01; FIG. 6).

Example 2

Animal Preparations

The male mice (ICR strain) weighting 18-20 g were housed at 22±1° C., under a 12 h light-dark cycle with food and water available ad libitum. Animals were habituated to the housing conditions for one week prior to the experiments. Behavioral testing was carried out during the light portion of the cycle. The experimental protocols were approved by the Hospital Animal Research Committee of National Taiwan University Hospital.

Isolation and Preparation of Tea Polyphenols

TP (tea polyphenol) was isolated according to the procedure described in example 1.

Statistic

Statistical comparisons between study groups were performed using one-way ANOVA test followed by post hoc multiple comparison with Dunnett's test. Factors are different groups. In comparing seizure frequency, Chi square tests were performed. P values of less than 0.05 were considered to be statistically significant.

Seizure Score

In NMDA-treated mice, seizures developed through a sequence of paroxysmal scratching, hypermotility and aircling, tonic-clonic convulsions and, occasionally, death. The following semi-quantitative scale was used for the examination of excitotoxic severity: 0, no response; 1, excessive grooming plus paroxysmal scratching; 2, mild hypermotility; 3, extensive hypermotility and circling; 4, forepaw clonus plus tail hypertonus; 5, generalized tonic-clonic convulsions; 6, "status epilepticus" and death (Marganella et al. 2005. Comparative effects of levobupivacaine and racemic bupivacaine on excitotoxic neuronal death in culture and N-methyl-D-aspartate-induced seizures in mice. Eur. J. Pharmacol. 518: 111-115). The latency (in sec) for generalized (clonic or tonic-clonic convulsions) seizures was also determined.

Result:

Neuroprotective Effects of TPM (Tea Polyphenol Plus Memantine) Against NMDA Excitotoxicity in Different Dosage Regimens In this example, the combination of TP with M (memantine) in three different dosage ratios of 6:1, 3:1, and 10:1 respectively; these are TPM6 (TP 30 mg/kg/day:M 5 mg/kg/day), TPM3 (TP 15 mg/kg/day:M 5 mg/kg/day) and TPM10 (TP 30 mg/kg/day:M 3 mg/kg/day), respectively. Their neuroprotective effects were evaluated after pretreatment for fourteen days or one day prior to the intracerebroventricular injection (icy) of 8 mM NMDA (3 µl). The results showed that attenuations of NMDA-induced seizure scores in percentage by M, TPM6, TPM3 and TPM10 were by 60±10%, 50±12%, 60±13% and 70±10% respectively, as compared with the control vehicle 90±10%. It appeared that the drugs treatments were all effectively in decreasing NMDA-induced excitotoxic seizures and TPM10 apparently was superior to M alone or TPM6 or TPM3.

Locomotor Activity Test

Mice were individually placed in an open field and performed in a separated room with no interference noise or human activity as described previously (Chuu et al. 2001. Abnormal auditory brainstem responses for mice treated with mercurial compounds: involvement of excessive nitric oxide. Toxicology 162: 11-22.). A large colorless rectangular box with a metallic grid floor was used (70-cm wide, 90-cm long and 60-cm high). The photobeam activity monitors (TruScan coulbourn instruments) was used for measuring real-time X-Y activity track-type plots. Overall pulses were measured in an electromechanical counter as a gross measure of activity and recorded by a PC. Each mouse was allowed to move freely for 5 min but data were not scored, and then the number of squares crossed and the plots of tracking were counted during a period of 30 min for all experiments and quantification of data was by TruScan99 software.

Elevated Plus Maze

For testing, mice were individually placed in the center of the maze facing a closed arm and allowed 5 min of free exploration. The number of entries into open arms, the number of entries into closed arms, and the total time spent in the open arms and total time spent in the closed arms were measured. Entry was defined as all four paws in the arms.

Rotarod Motor Equilibrium Performance on Rotarod

Mice were tested for their ability to balance on a slowly rotating rod (60 revolutions per min) as described previously (Chuu et al. 2001. Abnormal auditory brainstem responses for mice treated with mercurial compounds: involvement of excessive nitric oxide. Toxicology 162: 11-22.). One day before the experiment, mice were tested through ten consecutive sessions to stay on the rod and reach the cut off time of 180 s. One day after injection, mice were tested again. The retention time, defined as total time (sec) remaining on the rod, was recorded at each session.

Results:

Effects on Locomotor Activities

As shown in FIG. 7, memantine (10 mg/kg/day) for consecutive 14 days increased locomotor activities in the open field, while TPM6 and TPM3 only slightly increased and TPM10 had no effect on the locomotor activities. After icy injection of 3 µl of 8 mM NMDA markedly decreased locomotor activities which were prevented by pretreatment with M or TPM. Estimation of the neuroprotective potencies against NMDA-decreased locomotor activities was in the order TPM10>TPM6>TPM3>M (FIG. 8A). As to the neuroprotective effects against the decreased jump exploratory effect of NMDA (FIG. 8B), the order of the potencies were M>TPM6>TPM3>TPM10. However, after pretreatment with M and TPM alone for consecutive 14 days, the decrease in jump activity in orders are TPM6>M>TPM10, but TPM3 did not affect the jump activities (FIG. 8B). In addition, NMDA increased the retention time in the open field of the elevated plus maze but decreased rotarod motor equilibrium function which could be most efficiently prevented by TPM10 (FIGS. 8C and 8D). It was noted that prolonged use of M alone prominently increased retention time in the open field of elevated plus maze and reduced the motor equilibrium function similarly to NMDA (FIGS. 8C and 8D). Both TPM6 and TPM3 only slightly inhibited NMDA in open field and completely prevented NMDA-induced disturbance in motor equilibrium function (FIG. 8D). On the other hand, treatment of the drugs for one day and then icy injection of NMDA, the excitotoxic effects of the NMDA were persistent and the neuroprotective effects of the drugs were investigated by administration for consecutive 14 days following NMDA administration (FIG. 9). The comparative neuroprotective effects of the different dosage regimens were shown in FIG. 10A-10D. The decreased locomotor activities induced by NMDA could be partially reversed by M and TPM6, while TPM3 and TPM10 appeared to completely reverse and then further increase excitatory effects by achieving to 120% of the control (FIG. 10A). The decrease in jump activity induced by NMDA could be partially reversed by M and TPM6, while TPM3 reversed over to 160% and TPM10 exhibited the optimal neuroprotection reaching to the control level (FIG. 10B). Similarly, the increased retention time in the opened plus maze by NMDA was attenuated the best by TPM3, followed in order by TPM6, TPM10 and then M (FIG. 10C). The disturbance in rotarod motor equilibrium function induced by NMDA could be reversed by M and TPM10 but not by TPM6 and TPM3 (FIG. 10D).

Biochemical Analysis of Brain Tissues a. Preparation of Synaptosomes

The mice were sacrificed by rapid decapitation under anesthesia. The brain was dissected into four parts: cerebral cortex (CC), striatum (St), cerebellar cortex (CB), and brain stem (BS). Synaptosomes were prepared essentially as described in example 1. Briefly, different regions of the brain were removed and placed on ice. Specimens with the same areas and treatment conditions were subjected to homogenization on ice in 10 volumes of 0.32 M sucrose. Homogenates were centrifuged at 4° C. for 10 min at 600×g. The supernatant was then diluted 1:1 with 1.3 M sucrose to obtain a suspension with a final sucrose concentration of 0.8 M. This suspension was subjected to centrifugation at 20,000 g for 30 min at 4° C., yielding a myelin-rich supernatant and a pellet consisting of synaptosomes free of myelin. The supernatant was discarded, and the pellet was resuspended in 0.32 M sucrose buffer (pH 7.4). Synaptosomes were held on ice, usually for 15-20 min, until experiments were performed. The concentration of synaptosomes used for the experiments was corrected as mg proteins. The neurobiological and behavioral measures were taken on the same mice.

b. Measurements of $Na^+$, $K^+$-ATPase Activity

ATPase activities were determined by measuring the amount of inorganic phosphate (Pi) released from the substrate ATP according to a previously described colorimetric method. The method permitted the quantification of $Na^+$, $K^+$-ATPase and $Mg^{2+}$-ATPase activities in the same sample. Briefly, ATPase reactions were initiated in a mixture containing NaCl (354 mM), KCl (14.4 mM), MgCl2 (3.6 mM), $NaHCO_3$ (37.5 mM), ethyleneglycol bis(amino-ethylether) tetraacetate (EGTA, 1.5 mM), glucose (33.3 mM) and ATP (9 mM), and in the absence or presence of ouabain (1 mM). Synaptosomes prepared from different brain areas were incubated at 37±0.5° C. for 30 min in the reaction mixture. Reactions were terminated by the addition of 150 µl of a solution containing ammonium molybdate (1.05%), malachite green hydrochloride (0.034%) and Triton-X (0.6%). To stabilize the color reaction, 10 ml of a sodium citrate solution (34%) was added, and the assay solution was held at room temperature for 20 min. The optical density at 630 nm was determined by an ELISA reader (Dynatech MR-7000). The absorbance values obtained were converted to activity values by linear regression using a standard curve for sodium monobasic phosphate included in the assay at various concentrations. Pi released (in mmol/l) was taken to represent the concentration of inorganic phosphate released by the enzymatic hydrolysis of ATP. $Na^+$, $K^+$-specific ATPase activity was determined by subtracting ouabain-insensitive $Mg^{2+}$-ATPase activity from total $Na^+$, $K^+$- and $Mg^{2+}$-ATPase activities. Protein concentration was determined colorimetrically with a commercial bicinchoninic acid kit (Pierce, Rockford, Ill.).

c. Mitochondrial Membrane Potential

Mitochondrial membrane potential ($\Delta\Psi m$) was measured using the fluorescent dye 3,3'-dihexyloxacarbocyanine iodide [DiOC(6)]. Synaptosomes were prepared as described above and diluted 1:40 in sucrose buffer, followed by addition of DiOC(6) to a final concentration of 1.5 µM. After 20 min of incubation at 37° C., fluorescence was measured in a Microplate Fluorometer (Labsystems, Helsinki, Finland) (excitation wavelength: 484 nm; emission wavelength: 501 nm).

d. Assessment of Mitochondrial Metabolic Function

Mitochondrial metabolic function was assessed by the conversion of the dye methylthiazoletetrazolium (MTT) to purple formazan. This assay is based on the ability of mitochondrial succinate reductase to metabolize MTT to formazan; this reaction takes place only in functionally intact mitochondria. Synaptosomes were prepared as described above. 100 µl of the synaptosome suspension and 50 µl of 5.0 mg/ml solution of MTT in 0.32 M sucrose buffer were added to each tube. The samples were incubated for 120 min at 37° C. The purple formazan crystals were pelleted by centrifugation and the supernatant discarded. The pellets were dissolved in dimethylsulfoxide and transferred to 96-well microplates. The formation of formazan was quantitated spectrophotometrically at 570 nm using a Microplate Reader.

e. Nitric Oxide Detection

The brainstems used herein were weighed and homogenized in 10% (w/v) of homogenate buffer (10% sucrose buffer), and then centrifuged at 0° C. for 20 min at 10000×g. To avoid incomplete protein denaturation, we added 70% ethanol into the tissue pellet and also the blood sample, and allowed the mix to stand overnight. On the following day, all samples were centrifuged at 4±0° C. for 2 min at 12000×g, the supernatants from the brainstem tissue and the whole blood being collected and assayed by a NO/ozone chemiluminescence assay method (NO-Analyzer 280A, Sievers Research Inc., Boulder, Colo., USA) for quantitative NO assay. Briefly, we measured the oxidation products nitrite ($NO*2$) of NO using a reaction vessel containing a reducing system (0.1 M vanadium chloride, Aldrich Co., Germany). The detection of NO is completed by its reaction with ozone, which leads to the emission of red light ($NO+O_3 \rightarrow NO*2+O_2$; $NO*2 \rightarrow NO_2+h\nu$). The linearity of the standard curve was confirmed with 1, 5, 10, 15 and 20 µM NO, these being prepared using freshly-prepared solutions of $NaNO_2$ (10 µl) in distilled water. The brainstems of the Hg treated mice were acquired and homogenized for the purposes of the determination of $NO_x$ ($NO^-_2$ plus$^-_3$) levels immediately, 5 and 11 weeks subsequent to the cessation of Hg administration.

Results

As shown in FIGS. 11A and 11B, NMDA decreased mitochondrial reductase (MTT) and nitroblue tetrazolium (NBT) activities, which could be better reversed by administration of TPM10 and TPM6 followed by M and TPM3. The mitochondrial membrane potential was slightly decreased by NMDA which was elevated by TPM10 and M to the normal control level but unaltered by TPM6 and TPM3 (FIG. 11C). The decrease in $Na^+$—$K^+$-ATPase activities (the most sensitive biomarker to reactive oxygen species) by NMDA could be reversed by TPM3 and TPM10 followed by TPM6 but not by M (FIG. 11D). The NO levels of brain synaptosomes were increased by NMDA which was also reversed by TPM3 and TPM10 but decreased by M and TPM6 respectively (FIG. 11E).

Memantine is currently recognized as a useful clinical drug for improving cognition function of Alzheimer disease patients. However, the side effects of long term administration of memantine such as hallucination, delusion and psychosis should be awared for combating. Examples 1 and 2 confirmed the fact that tea polyphenol could not only be neuroprotective but also potentiate memantine against NMDA neurotoxicities. Furthermore, a better dosage ratio of TP and M (TPM10, TP 30 mg/kg/day, M 3 mg/kg/day, the dose ratio is 10:1) have been designed. TPM10 by itself did not affect the normal neurobehavioral activities but it could exhibit the best potential efficacies against NMDA excitotoxicities after long term administration, suggesting that TPM10 possessed a beneficial property for management of neurodegenerative diseases such as Alzheimer's disease. Because both M and TP are currently clinical useful drugs, this novel regimen TPM10 would be safe and exhibited a promising composition in increasing therapeutic efficacies and attenuating adverse effects of M for clinical patients.

What is claimed is:

1. A method for treating a subject suffering from a disease or condition associated with excitotoxicity, comprising administering to the subject a therapeutically effective amount of a composition comprising memantine and a green tea polyphenol mixture in combination, wherein the ratio of the green tea polyphenol mixture and memantine is from 3:1 to 10:1, whereby the composition provides synergistic neuroprotective effect to the subject.

2. The method according to claim 1, wherein said treating is made by attenuating mitochondria dysfunction associated with loss of $Ca^{2+}$ homeostasis and enhanced cellular oxidative stress.

3. The method according to claim 1, wherein said disease or condition is a neurodegenerative disease or condition.

4. The method according to claim 3, wherein said neurodegenerative disease or condition is brain trauma, brain ischemia, epilepsy, or Alzheimer's disease.

5. The method according to claim 1, wherein said excitotoxicity is caused by NMDA receptor over-activation.

6. The method according to claim 1, wherein said subject is human.

* * * * *